United States Patent [19]

Müller et al.

[11] Patent Number: 4,960,994
[45] Date of Patent: Oct. 2, 1990

[54] X-RAY CASSETTE FOR SHEET X-RAY RECEIVING MATERIAL AND METHOD OF PROCESSING THE SAME

[75] Inventors: Jürgen Müller, Munich, Fed. Rep. of Germany; Manfred Schmidt, Kirchheim, Fed. Rep. of Germany; Dieter Wauer, Taufkirchen, Fed. Rep. of Germany; Thomas Zehetmaier, Neufarn, Fed. Rep. of Germany; Georges Brys, Beverenwaas, Belgium; Emile Schoeters, Lier, Belgium; Werner Haug; Walter Bauer, both of Munich, Fed. Rep. of Germany

[73] Assignee: Agfa-Gevaert AG, Leverkusen, Fed. Rep. of Germany

[21] Appl. No.: 238,035

[22] Filed: Aug. 29, 1988

[30] Foreign Application Priority Data

Sep. 17, 1987 [DE] Fed. Rep. of Germany ....... 3731204

[51] Int. Cl.⁵ .............................................. A61B 6/00
[52] U.S. Cl. ................................. 250/327.2; 378/165
[58] Field of Search ............... 250/327.2 A, 327.2 R, 250/327.2 B, 327.2 C, 482.1, 484.1 R; 378/162, 165, 182–185

[56] References Cited

U.S. PATENT DOCUMENTS 4,739,480  4/1988  Oono et al. ..................... 378/165

FOREIGN PATENT DOCUMENTS 0142709  5/1985  European Pat. Off. .
0079557  4/1986  European Pat. Off. .

Primary Examiner—Janice A. Howell
Assistant Examiner—Richard Hanig
Attorney, Agent, or Firm—Michael J. Striker

[57] ABSTRACT

A cassette for an x-ray film coated with a stimulable phosphor layer is formed so that a cassette memory which carries storable, recordable, readable and erasable data is rigidly attached to the cassette at the positioned spaced a predetermined distance from a given cassette corner. This position is the same for all cassettes of the same type and different formats.

16 Claims, 3 Drawing Sheets

X-RAY CASSETTE FOR SHEET X-RAY RECEIVING MATERIAL AND METHOD OF PROCESSING THE SAME

BACKGROUND OF THE INVENTION

The present invention relates to an X-ray cassette for X-ray sensitive sheet-like material, preferably for a film coated with a stimulable phosphor layer and a method of processing such a cassette.

A cassette of the foregoing type has been disclosed, for example in EP No. 0,079,557 B1 while a method of handling such a cassette by means of devices available on the market has been disclosed in EP No. 0,142,709 A2.

The known cassette with a photographic material is distinguished by that the photographic material has an identification means which are rigidly attached to that material. Furthermore, such a cassette has an opening which is made in conformity with the identification means so that the identification of the cassette is possible from its outer side. Thereby the identification means can be formed by a magnetic indication medium on which or by which identification data can be magnetically indicated or scanned. The advantage of such a cassette resides in that identification data are applied directly on the photographic material non-separately from it and thus can not be lost, and yet these identification data can be applied from outside or scanned. Suitable methods and devices for using such a cassette with the phosphorus-coated film are substantially such that, upon the exposure of the film positioned in the cassette with X-rays a latent image is produced. The latent image is brought to luminescence in the reading station after being removed from the cassette by means of a laser scanner (the phosphorus is stimulated) and the latent image is converted into digital electric image signals which can be converted into a visible image on the screen or image screen receiving apparatus or a computer-controlled laser beam receiving apparatus. Then the remaining image is erased and the film is re-turned into the cassette-leading apparatus. The identification data on the identification means of the film should be thereby read-out by a suitable reading apparatus and converted into digital electric identification signals and added to the aforementioned digital image signals. On the other hand, after erasing of the latent image from the film the image signals are useless. The cassettes which are transported from the reading station separately from the films have no identification means or data which can be used for re-loading of the cassettes in the re-loading apparatus.

The disadvantage of such known X-ray cassettes having films with the layer of the stimulable phosphor resides in that the cassette must have a non-closable window for identification means located on the film side. If an incorrect film is inserted it becomes exposed at the location of the window which would result in an "erased" film which can not be used for receiving the image, or the identification means can not be read out if they are positioned on the side of the film, which faces away from the phosphorus layer. Furthermore, the manufacture of the cassette with a window is more expensive than the cassette that has no opening. Further, despite the window in the cassette the reading device for the identification means should be provided in the reading station because otherwise digital image signals and identification signals can not be combined and the data on the film would not be useful anyway. The disadvantage of the known method resides in that the film between being removed from the cassette in the reading station and the reinsertion into the cassette in the cassette-loading apparatus is not protected against mechanical influence so that the phosphor layer can be subject to wear and/or damage.

SUMMARY OF THE INVENTION

It is an object of the present invention to provide an improved X-ray cassette for a film having a stimulable phosphor layer thereon.

It is another object of the invention to provide a cassette without a non-protected opening but having nevertheless identification data convertible into digital electric signals and storable with digital image signals of a latent image on the film.

Yet another object of the invention is to provide an improved method of processing an X-ray cassette with a film having a stimulable phosphor layer thereon.

These and other objects of the invention are attained by a cassette for an X-ray sensitive sheet-like material, comprising a memory rigidly attached to the cassette and located in a position spaced by a given distance from a predetermined corner of the cassette, which is the same for all cassettes of the same type but different format, said memory carrying storable, recordable, readable and erasable data in digital form.

Said memory may be a semiconductor memory with a galvanic data transmission.

The cassette may further include a carrier plate supporting on a side thereof, which faces an external side of the cassette, said semiconductor memory.

Galvanic contact elements (K1 to K4) may be provided on an external side of said carrier plate opposite to the side which supports said memory.

The cassette may be formed with a recess in which said carrier plate is inserted.

An external surface of said carrier plate may be in alignment with a plane of the external side of the cassette.

The external surface of said carrier plate may extend somewhat below a plane of the external side of the cassette.

A respective cassette format and a utilizable photographic material format may be stored in a non-erasable, protected data set or memory portion of said memory, or in other words in a write-protect portion.

A type of a photographic material may be stored in a data set of said memory and is protected therein against a non-desired erasing.

Said photographic material may be a film coated with a stimulable phosphor layer, said memory having a changeable data set or memory portion, or in other words a write enable portion, by which a number of exposures and evaluations and erasings of said film is countable and which is reset to zero when a film in the cassette is exchanged.

The objects of the invention are also attained by a method of processing a cassette which carries a photographic film coated with a stimulable phosphor layer and which includes a memory carrying storable, recordable, readable and erasable data in digital form, the method comprising the steps of exposing said film to X-rays to produce a latent image in a reading station, after removing said film from the cassette, stimulating said latent image by means of a laser scanner and converting said image into digital electric image signals, exposing said film to a suitable light containing no X-rays to erase said film, storing said digital image signals in a central memory, receiving on a photographic sheet film a converted image visible on an image screen or an image in an image screen receiving apparatus or in laser beam receiving apparatus controlled by said central memory, providing an identification station with an operation keyboard and storing data specific for an X-ray reception of said cassette memory in said identification station, reading-out the data stored in said cassette memory in the reading station and storing said data together with said digital image signals of said exposed film in said central memory, and reproducing the image together with a respective image appearing on the image screen or image screen receiving apparatus on the photographic sheet film.

The film after being exposed to X-rays may be evaluated in a reading apparatus and wherein said film, after being removed from the cassette in said reading station and after converting said latent image into said digital image signals and erasing the image, is returned into the same cassette which is discharged from the reading station.

The erasing of specific non-changeable data of said cassette memory may be executed either after storing in the reading station or during a new recording of changeable data of the cassette memory in the identification station.

A number in a changeable data set of said cassette memory serving for counting cassette or film exposures may be increased by one at each data reading-out and storing in said reading station so that said data set contains an entire number of exposures made on the film contained in the cassette.

The entire number of exposures of the film positioned in the cassette may be automatically read-out in the identification station and the reading station, and upon exceeding the greatest number allowed for a good exposure result, an alarm signal is released in said identification station or said reading station.

During the insertion of a new film into the cassette, the changeable data set may be reset to zero in said identification station.

The cassette and the film in said reading station may be separately processed after the storing of said digital image signals together with the data of the cassette memory in said central memory, and the cassette released from the film is discharged from the reading station and fed into a cassette loading device; the method further including providing in said reading station film supply magazines (6g) for films of different formats and types, controlling data indicative of a cassette and film format and type stored in said cassette memory in said central memory, and moving a film removed from the cassette into a respective film supply magazine in accordance with a format and a type of the film.

Different film supply magazines provided with film packs in the reading station may be placed into the cassette-loading devices, each being placed into such a device that a cassette to be loaded is positioned in a respective loading device, and wherein format and type data of the film are read-out by a cassette memory reading device and are passed to a loading control device by which a respective film supply magazine for re-loading the cassette is supplied, and wherein the cassette loaded with the film in accordance with the data of the cassette memory is closed and removed from the loading device.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 3:
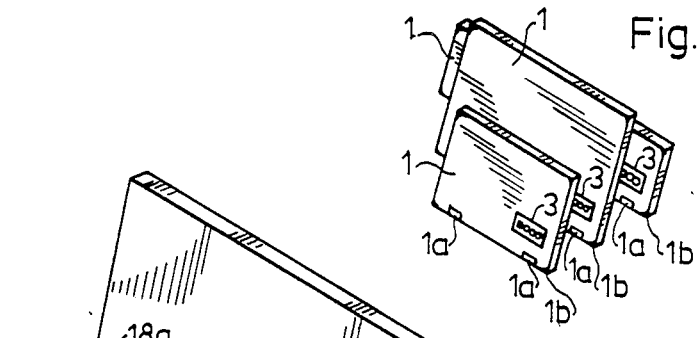
FIG. 3 is a perspective view of the cassettes of the invention of various formats.

The invention concerns widely known X-ray cassettes for flat X-ray-sensitive photographic materials. Such cassettes are comprised of two housing parts pivotally connected to each other. One of the housing parts is a bottom part while the other one is a lid, whereby normally the bottom part faces a patient or X-rays. A bonding agent for photographic material, for example a foam plate is positioned in such a cassette. These cassettes are shown in the drawings only schematically and are identified with reference numeral 1. Each cassette is provided with known locking and unlocking elements 1a (FIG. 3) for locking and unlocking the lid and are available for different sizes or formats. FIG. 3 shows three formats of the cassettes. In particular, a photographic or image-receiving film 2 coated with a layer of a stimulable phosphor, and not a usual photographic X-ray film, is positioned in each cassette 1. A latent image which is produced by scanning by a laser beam and is converted into a digital electric image signal and stored, appears on said layer during the exposure with X-ray beams. The stored image signals may have then observed as a visible image on a screen. Accordingly, a so-called hardcopy on the customary photographic film is produced by known methods. However the utilization of the cassette which will be described herein below for known photographic X-ray films is not excluded.

A storage or memory 3 is placed instead of the bottom flat side of each cassette on the outer face of the lid in a predetermined position relative to a reference point which is the same for all cassettes of the same type but different formats. This storage or memory which stores, describes, reads and erases data in a digital form is connected to the upper face of the cassette lid. Storage 3 is formed as a unit and is identified as a cassette storage to distinguish the same from other memories. A predetermined 10 cassette corner 1b (FIG. 3) can serve as a reference point for the position of the cassette storage 3. This corner is positioned at the same location in a corresponding device in the processing apparatus for the cassette 1 for the cassettes of all formats. This relation between the location of the cassette storage 3 and corner 1b of the cassettes of all formats is clearly seen in FIG. 3.

A magnetic memory (magnetic strips) or a semiconductor memory can be used as a cassette storage 3. Magnetic memories have the advantage that they are simple and inexpensive. However they can store only a few data and a reading-out process is relatively long. Thus semiconductor memories are preferable. The advantage of semiconductor memories resides in a quick readability, high storage capacity, non-sensitivity to magnetic fields and they require a relatively small amount of mechanisms for a reading-out process. In case of use of galvanic contacts a series of memories with a small number of connections are preferable.

Figure 4:
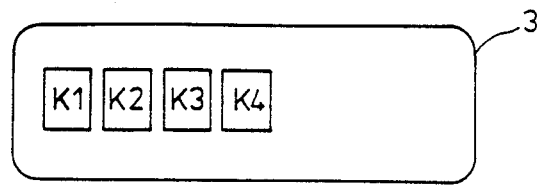
FIG. 4 is a plan view of the memory for the cassette according to the invention.
Figure 5:
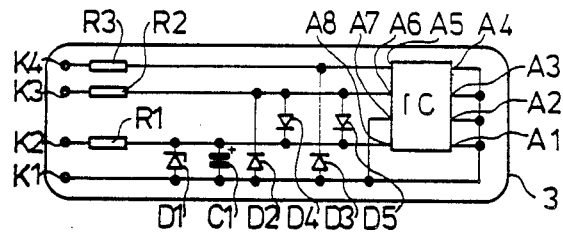
FIG. 5 is a plan view of the backside of the memory of the cassette, which faces the outer side of the cassette.

Referring now to FIGS. 4 and 5 it will be seen that a cassette storage 3, which should be adjusted in a data input, data reading-out, data-erasing to the cassette in which such a storage is used, includes a supporting or carrier plate also identified at 3. As shown in FIG. 5, a memory chip 1C is positioned on the side of plate 3, which faces the cassette flat side. Memory chip 1C is protected against damage in the known fashion by additional passive electronic structural components. Component or element D1 in connection with resistor R1 screens against high maintenance voltage at contact K2. Capacitor C1 serves to intercept possible short-time voltage breaks due to bad contacts. Elements D2 and D4 in connection with resistor R2 protect contact A6 of the memory chip 1C. This memory chip has eight connections A1 to A8. Remaining elements D3, D5 and R3 have similar functions. Four contacts K1 to K4 (also shown as terminals in FIG. 4) terminate on the upper side of the memory chip to be connected to the contacts of the device which is connected with the memory chip; namely K1 is connected to the ground, K2 to the voltage supply (+5V), K3 to the time input for synchronizing the data flux and K4 serves as a serial data input and data output. A galvanically contacting EEPROM can be utilized, for example as the memory chip.

The circuit is applied in SMD-technology (surface mounted devices) to the side of the conductive plate coated with paper at two sides, which side faces a user. Four through contacts lead to four gold-plated contact surfaces K1 to K4 on the upper side. The memory 1C is electrically connected with a reading-out and recording electronics with the aid of the contacting technology so that EEPROM can respond to a correct protocol to send and receive correct informations. A known 11C-Bus-Protocol (11C-BUS:INTER-1C-BUS) is used for transfer; a memory block of various makers can be used with this 11C-BUS-Protocol.

The 11C-BUS-Protocol ensures that (also with applied maintenance voltage) a non-desired programming of the EEPROM is prevented. Since in fact, the 1C outside the recording-reading device has no current almost one hundred percent of data safety is ensured. Eventually errors due to fallen out bits, which manufacturers expect in first 10,100 programmings, can be easily recognized and corrected by a respective coding. The programs in all reading and recording devices can be written in such a way that each input is automatically completed by suitable control sums, and with each reading the possibility of errors is checked. Depending on the type of an error it can be corrected, unnoticably for a user, or an error message can be issued, which for example would direct the user's attention to the erroneous cassette. The user can manually eliminate an error or replace the cassette. The carrier plate 3 may be inserted in a recess formed in the external side of the cassette so that the outer side of the carrier plate would be either flush with the plane of the external surface of the cassette or lie somewhat deeper than that external surface. Thereby the danger of the non-desired touching of contacts K1 to K4 would be avoided.

It is also possible in the aforedescribed embodiment that the format of a respective cassette and thus a film format of the film contained therein would be stored, for example by a manufacturer, in a non-erasable protected data set of the cassette memory 3. In a further data set of the memory 3, the type of the photographic material contained in the cassette can be stored by either the manufacturer or a user in accordance with a given process of handling of the cassette to protect against non-intended erasing.

Finally, depending on the desired handling it is advantageous if an interchangeable data set would be provided in the memory 3. Such a data set would enable to count the number of exposures or reevaluations or erasings in the film 2 contained in the cassette and, upon the exchange of the film in the cassette 1 to reset the number back to zero.

The use of cassette 1 of the aforedescribed type with the phosphorus-coated film 2 and the recording and at least partially erasable memory 3 rigidly attached to the flat side of the cassette renders possible a method with various operations This method is based, firstly on the known principle of handling of phosphorus-coated films 2, wherein with the exposure of film 2 with X-rays in an X-ray apparatus 5 (FIG. 1) a produced latent image in a reading station 6 is stimulated, after the removal of film 2 from the cassette 1, by means of a laser scanner 6a via a rotating mirror 6b, preferably upon a further movement of film 2, so that the image due to luminescence is converted by a fibrooptics and photomultiplier 6c into digital electric image-responsive signals, and the remaining image on the film 2 is erased by an exposure to visible light by means of a lamp 6d. Digital image-responsive signals are stored in a central memory 7 and can here again be converted into an image visible on a screen 8 or received in an image screening photographic apparatus or a laser machine (both devices are known as hardcopy devices), on a photographic sheet material as a visible image. These images can be however also stored in disks 10 or the like, for copies.

A new method principle for processing the cassette 1, 2, 3 according to the invention resides in that in the identification station 4 provided with an operation keyboard 4a specific image data (for example patient data) for a specific X-ray receiver are stored in the cassette memory 3 and either directly before or after the X-ray exposure in the X-ray apparatus 5 these specific image data stored in the memory 3 are read-out in the reading station and together with digital image signals of the film 2 exposed to X-rays in the cassette 1 are stored in the central memory 7 or are photographed together with a respective image visible in the hard copy device 9. The erasing of the specific image data in the cassette memory 3, after the evaluation in the reading station 6, can be executed either in a recording device 6e for the cassette memory 3 in the reading or recording station 6 or, upon a new introduction of the cassette memory 3, in the identification station 4. These variants of the method depend upon the structure of the apparatus.

Figure 6:
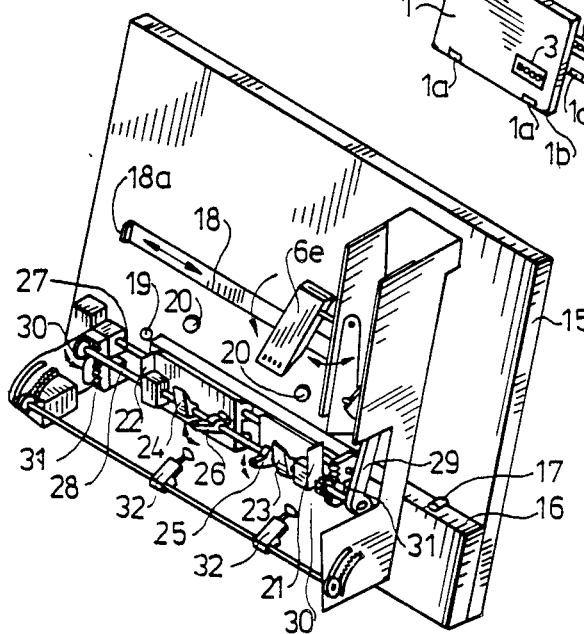
FIG. 6 is a perspective view of the device for loading and unloading of the cassette according to the invention with a device for reading the memory of the cassette.

Two different methods of handling the cassette 1 according to the invention are based on the aforedescribed principle. One of these methods is illustrated in the schematic representation in FIG. 1. Cassette 1 exposed and provided with stored specific image data is inserted into the reading station 6 and positioned therein so that specific image data are read-out from the cassette memory 3 by the reading device 6e; then film 2 is removed from the cassette 1, and the film 2, after the aforedescribed conversion of the latent image contained therein into digital image signals, is transported back. Since a series of constructive possibilities exist for the realization of this process and the transport means for transporting the film 2 through the scanning and erasing devices 6a to 6d are known such transport means for film 2 in the reading station 6 is schematically shown as a transporting tape. For positioning the cassette 1, opening of this cassette, removal of film 2 and re-insertion of film 2 into the same cassette 1, closing of the latter and removal of the cassette from the reading station, are used conventional devices known in cassette loading and cassette unloading apparatus. One substantially known device for executing the process of the invention is shown in FIG. 6 and will be described in detail below.

The most important feature of this system is that film 2 and cassette 1 are combined into a single unit and are separated from each other in the reading station 6 only for scanning and conversion into digital signals. The cassettes can be opened by a user; this is not however provided because the film should not be preliminarily exposed to light which can penetrate the cassette in such a case. Should the film be once inserted the correspondence of the film to the cassette is not ensured. This correspondence (at least from the X-ray exposure to the conversion of the image into the digital signal) is the condition for the above-described method of the data storage on the cassette.

Figure 1:
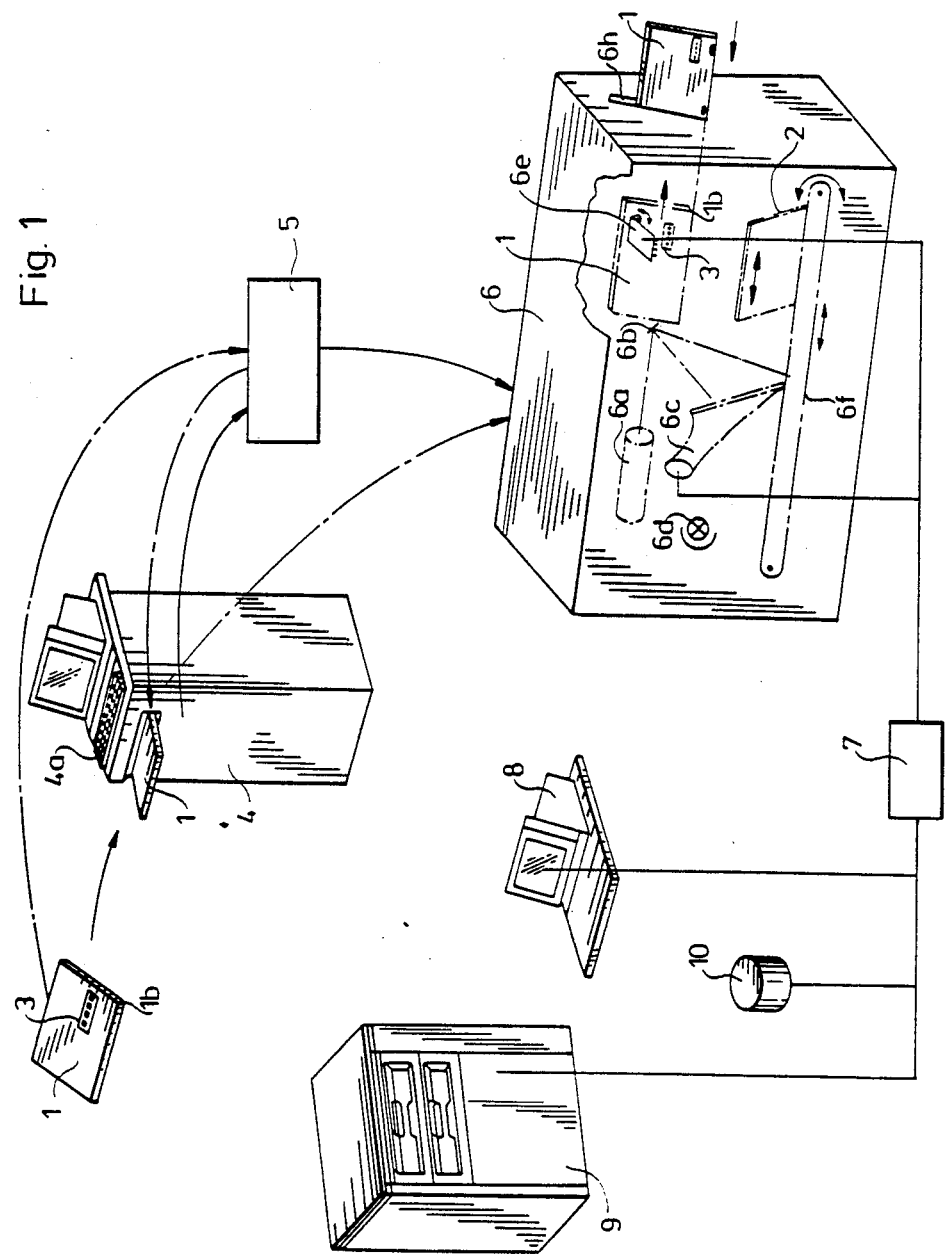
FIG. 1 is a schematic view of the combination of the devices for carrying out a method of handling a cassette according to the invention.

The method of handling of the cassette shown in FIG. 1 has the following advantages:

1. A user has no contact with the film. He or she does not examine the film except when the film, after a long use, should be replaced.

2. A specific cassette-loading process with a cassette-loading device is dispensed with.

3. It can be always assumed that the cassette is filled.

4. The method offers many possibilities, with a selection of a medium for data storage because a great deal of space is available on the cassette and on the film as well.

5. The cassette can be entirely closed and should have no window for reading the data.

6. The film and the cassette should be provided over the entire service life thereby with a variable data set. This offers the possibility that the age of the cassette and film, the number of exposures as well as the condition "exposed/erased" be recognized. The inducement of the pre-counting from "one" in the cassette memory 3 with each digital conversion of the latent image can be executed in the reading station 6 by the reading device 6e which is reset to "zero" when the film is exchanged in the identification station 4. For storing the film condition "exposed/erased" in the cassette memory 3 a data input device in the X-ray apparatus 5 and a corresponding erasing arrangement in the reading device 6e should be provided. Upon reaching the count which indicates the durability of the film a warning signal can be released in the reading station 6 or identification station 4.

7. Patient-related data are recorded on the cassette before or during the X-ray examination and they are accompanied with registered image informations.

8. No further information carrier, such as a data card, is necessary.

9. Control data for further processing are input already during the exposure without a direct contact with the reading station.

10. If different types of films are available the type of the film can also be stored in the cassette memory.

11. Due to the insertion of the film back in the same cassette in the reading station, the film must pass only a very short path outside the cassette, whereby a better protection against damage and wear during the transport of the film is provided than in other methods for the cassettes with phosphorus-coated films. This method is particularly practical when patient data are stored not in the memory of the cassette but digital image signals are added in another fashion, for example by the legible memory on the film, or data signals are added directly to image signals through the keyboard in the reading station.

Figure 2:
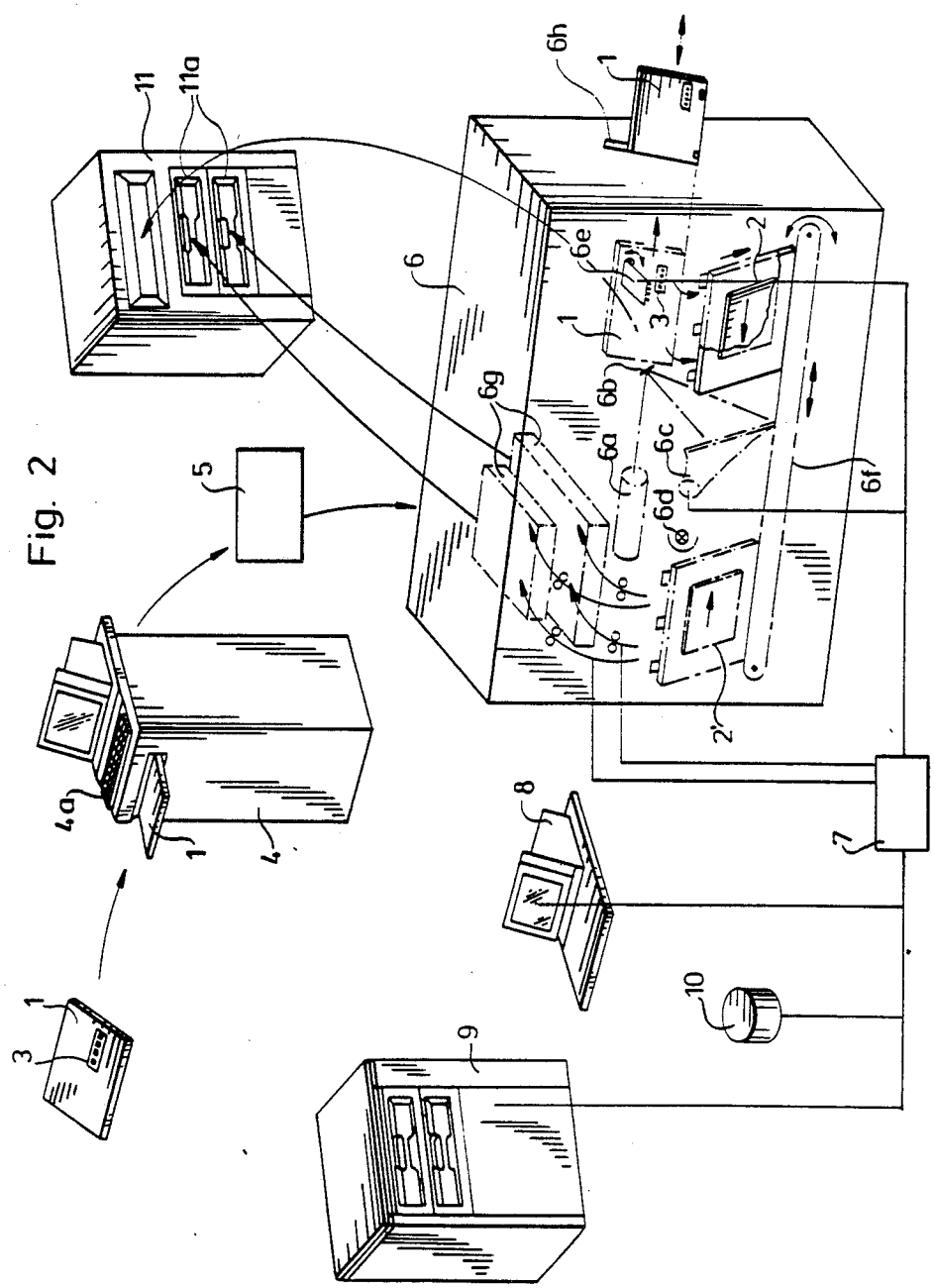
FIG. 2 is a schematic view of the combination of the devices for carrying out another possible method of handling a cassette of this invention.

The method of processing the cassette 1 of the invention shown in the diagrammatic view of FIG. 2 differs from that of FIG. 1 in that the cassette 1 in the reading station 6 and film 2, after the collective storing of digital image signals and cassette memory data in the central memory 7 are guided further separately from each other, that the emptied cassette 1 is removed from the reading station 6 and is transported in the known manner to a cassette-loading device 11 for a reloading, that film supply magazines 6g for different film formats and types are provided in the reading station 6, and that the scanned and erased film 2', removed from the cassette 1, after the data thereof have been stored in central memory 7, is transported by means of known transport means into a respective film supply magazine 6g in accordance with its format and/or type. If the film packs of the respective qualities are collected in the film supply magazines 6g the latter are inserted into respective drawers 11a of the loading device 11 for cassettes 1. A further reading device comparable to the reading device 6e must be provided in the loading device 11. Such reading device, upon the insertion of the cassette loaded with the memory 3, would read out the format and type of the film, and a respective cassette will be loaded from a proper film magazine, upon the signal issued by an electronic control device in a known fashion.

Also, with this cassette-processing method, film 2 must be moved back fully unprotected only over a very short path. By discharging the film into the film supply magazine 6g and transporting the film from the magazine to the cassette, a considerably greater wear can be caused than that in the method shown in FIG. 1. Advantages 2, 3, 6 and 11 out of eleven advantages of FIG. 1 can not be ensured in the method of FIG. 2.

Known transporting devices are utilized for transporting cassette 1 towards and within stations 4, 6, 11. These devices may be friction rollers, feeding rollers, transport tapes or belts or slides with grippers. Films 2 can be conveyed in the reading station 6 also in the known fashion to the cassette loading and unloading device, for example by suction heads or transport roller pairs, as shown in FIG. 2 for the transport of films from the position 2' into the individual film supply magazines. The positioning of cassettes for reading out the cassette memory 3 and for the removal of the exposed film and returning the same into the cassette in the reading station 6 according to FIG. 1 or the positioning and reloading of the emptied cassette in the loading device 11 can be carried out in each case by known arrangements disclosed, for example in the German publication No. DE 3,544,719 C1. The device disclosed in this publication is shown in FIG. 6 and can be employed in the present invention only as one of possible embodiments. This device includes a supporting and guiding plate 15 which is positioned laterally of and behind the cassette insertion slot 6h of the reading station 6. A guiding track 16 for the cassette is in alignment with the lower edge of the slot 6h as shown in FIG. 1. FIG. 6 further illustrates a drivable friction roller 17 on the guiding track 16. If the cassette 1 is inserted into the cassette will be gripped by this roller and moved to the transport belt or tape 18 with grippers 18a of which only one is shown FIG. 6. Now the transport tape 18 will transport the cassette up to the positioning device. When the front edge of the cassette reaches the light barrier 19 the cassette displacement is ceased. A number of identical plungers 20 which touch the cassette only slightly above the track 16 from the back side thereof push the cassette forwardly in the region of the positioning means. The latter are comprised of a rigid stop angle 21 and a displaceable angle 22 which is in alignment with angle 21. Between angles 21 and 22 are provided pivotal and displaceable bars or elements 23, 24 for unlocking the cassette lid and rotatable levers 25, 26 for closing the lid of the cassette. The stop angle 22, together with the bar 24 assigned thereto and lever 2b, is displaceable on its bar or rod 27 and, together with bar 23 and lever 25, is supported on a shaft 28 which is rotatable by a crank drive 29 rigidly connected thereto and is reciprocally displaceable by a gear 30 which meshes with a tooth rack 31 and is rigidly connected to the crank drive 29.

Upon the insertion of the cassette into the reading device 6, shaft 28 takes its upper position in which the nonrotatable angle pieces 21, 22 are positioned in or a little lower the plane of the track 16. The cassette is also displaced by plungers 20 from the track 16 in the region of angles 21, 22. Then the moveable angle 22 is displaced relative to the stationary angle 21 so that the cassette becomes positioned between angles 21 and 22. If now the 10 pivotable scanning device 6e positioned against the cassette lid pivots relative to the cassette memory 3 (FIG. 1) it scans the data stored therein and supplies these data to the central memory 7. The scanning device 6e then again is rotated forwardly and upwardly. Crank 29 now rotates shaft 28 in the counter clockwise direction. Thereby the cassette and the locking element and the lever are moved downwardly and, at the same time, bars 23, 24 and levers 25, 26 are rotated and also displaced so that the cassette locking arrangement 1a is unlocked and the cassette lid springs out again under the action of the respective spring and is pulled upwards on the opening hook hinged on the crank 29. By means of the known sucker 32 the film of the cassette is sucked out from the same and is guided further by means of the known transport device to the laser scanner 6a. After erasing the film the latter is conveyed back to the region of sucker 32 and is placed back into the cassette. Now the aforedescribed process is reversed by means of crank 29; the cassette and shaft 28 are transported upwardly, and levers 25, 26 engage the cassette lid and press it towards the cassette bottom. When the re-loaded and closed cassette is positioned with its lower edge lying in the plane of track 16 it is acted upon by non-shown plungers set opposite to plungers 20 which move it back on the track 16, and, by means of transporting tape 16, gripper 18a and friction roller 17, the cassette is removed through the insertion slot 6h from the reading device. The device shown in FIG. 6 is, of course, also suitable for the method illustrated in FIG. 2 without however the re-loading process for the cassette.

It will be understood that each of the elements described above, or two or more together, may also find a useful application in other types of X-ray cassettes and method of processing the same differing from the types described above.

While the invention has been illustrated and described as embodied in an X-ray cassette and a method of processing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A cassette for an X-ray sensitive sheet-like material, comprising a memory rigidly attached to the cassette and located in a position spaced by a given distance from a predetermined corner of the cassette, which is the same for all cassettes of the same type but different formats, said memory carrying storable, recordable, readable and erasable data in digital form, wherein said material is a film coated with a stimulable phosphor layer, said memory having a changeable memory portion by which a number of exposures and evaluations and erasings of said film is countable and which is reset to zero when a film in the cassette is exchanged.

2. A cassette for an X-ray sensitive sheet-like material, comprising a memory rigidly attached to the cassette and located in a position spaced by a given distance from a predetermined corner of the cassette, which is the same for all cassettes of the same type but different formats, said memory carrying storable, recordable, readable and erasable data in digital form, wherein said memory being a semiconductor memory with a galvanic data transmission.

3. The cassette as defined in claim 2, including a carrier plate, said semiconductor memory being provided on a side of said carrier plate which faces an external side of said cassette.

4. The cassette as defined in claim 3, wherein said galvanic contact elements are provided on the side of said carrier plate opposite to said side of said memory.

5. The cassette as defined in claim 3, wherein said cassette is formed with a recess in which said carrier plate is inserted.

6. The cassette as defined in claim 5, wherein an external surface of said carrier plate is in alignment with a plane of the external side of the cassette.

7. The cassette as defined in claim 5, wherein an external surface of said carrier plate is below a plane of the external side of the cassette.

8. The cassette as defined in claim 4, wherein a respective cassette format and a utilizable photographic material format are stored in a non-erasable, protected portion set of said memory.

9. The cassette as defined in claim 4, wherein a type of a photographic material is stored in a portion of said memory and is protected therein against a non-desired erasing.

10. A method of processing a cassette which contains a film coated with a stimulable phosphor layer and which includes a cassette memory carrying storable, recordable, readable and erasable data in digital form, the method comprising the steps of exposing said film to X-rays to produce a latent image in a reading station, after removing said film from the cassette, stimulating said latent image by means of a laser scanner and converting said image into digital electrical image signals, exposing said film to a suitable light containing no X-rays to erase said film, storing said digital image signals in a central memory, receiving on a photographic sheet film a converted image visible on an image screen or an image in an image screen receiving apparatus or in laser beam receiving apparatus controlled by said central memory, providing an identification station with an operation keyboard and storing data specific for an X-ray reception of said cassette memory in said identification station, reading-out the data stored in said cassette memory in the reading station and storing said data together with said digital image signals of said exposed film in said central memory, and reproducing the image together with a respective image appearing on the image screen or image screen receiving apparatus on the photographic sheet film, a number in a changeable data set of said cassette memory serving for counting cassette or film exposures being increased by one at each data reading-out and storing in said reading station so that said data set contains an entire number of exposures made on the film contained in the cassette.

11. A method as defined in claim 10, wherein the film after being exposed to X-rays is evaluated in a reading apparatus and wherein said film, after being removed from the cassette in said reading station and after converting said latent image into said digital image signals and erasing the image, is returned into the same cassette which is discharged from the reading station.

12. A method as defined in claim 10, wherein the erasing of specific changeable data of said cassette memory is executed either after storing in the reading station or during a new recording of changeable data of the cassette memory in the identification station.

13. A method as defined in claim 10, wherein the entire number of exposures of the film positioned in the cassette is automatically read-out in the identification station and the reading station, and upon exceeding the greatest number allowed for a good exposure result, an alarm signal is released in said identification station or said reading station.

14. A method as defined in claim 13, wherein during the insertion of a new film into the cassette the changeable data set is reset to zero in said identification station.

15. A method as defined in claim 10, wherein the cassette and the film in said reading station are separately processed after the storing of said digital image signals together with the data of the cassette memory in said central memory, and the cassette released from the film is discharged from the reading station and fed into a cassette-loading device; further including providing in said reading station film supply magazines for films of different formats and types, controlling data indicative of a cassette and film format and type stored in said cassette 11 memory in said central memory and moving a film removed from the cassette into a respective film supply magazine in accordance with a format and a type of the film.

16. A method as defined in claim 15, wherein different film supply magazines provided with film packs in the reading station are placed into the cassette-loading devices, each being placed into such a device that a cassette to be loaded is positioned in a respective loading device, and wherein format and type data of the film are read-out by a cassette memory reading device and are passed to a loading control device by which a respective film supply magazine for re-loading the cassette is supplied and wherein the cassette loaded with the film in accordance with the data of the cassette memory is closed and removed from the loading device.

* * * * *